(12) United States Patent  
Martin et al.

(10) Patent No.: US 8,287,909 B2
(45) Date of Patent: Oct. 16, 2012

(54) MEDICAL DEVICES CONTAINING MELT-BLOWN NON-WOVENS OF POLY-4-HYDROXYBUTYRATE AND COPOLYMERS THEREOF

(75) Inventors: David P. Martin, Arlington, MA (US); Said Rizk, Salem, NH (US); Kicherl Ho, Acton, MA (US); Simon F. Williams, Sherborn, MA (US)

(73) Assignee: Tepha, Inc., Lexington, MA (US)

( * ) Notice: Subject to any disclaimer, the term of this patent is extended or adjusted under 35 U.S.C. 154(b) by 736 days.

(21) Appl. No.: 12/336,755

(22) Filed: Dec. 17, 2008

(65) Prior Publication Data

US 2009/0162276 A1  Jun. 25, 2009

Related U.S. Application Data

(60) Provisional application No. 61/014,906, filed on Dec. 19, 2007.

(51) Int. Cl.
*A61K 9/14* (2006.01)
*A61K 13/00* (2006.01)
*A61B 18/18* (2006.01)
*A61B 17/56* (2006.01)

(52) U.S. Cl. .......... 424/489; 424/402; 424/423; 606/45; 606/76

(58) Field of Classification Search ........................ None
See application file for complete search history.

(56) References Cited

U.S. PATENT DOCUMENTS

| 5,527,341 | A | 6/1996 | Gogolewski et al. |
| 5,811,272 | A | 9/1998 | Snell et al. |
| 6,245,537 | B1 | 6/2001 | Williams et al. |
| 6,316,262 | B1 | 11/2001 | Huisman et al. |
| 6,323,010 | B1 | 11/2001 | Skraly et al. |
| 6,514,515 | B1 | 2/2003 | Williams |
| 6,548,569 | B1 | 4/2003 | Williams et al. |
| 6,555,123 | B2 | 4/2003 | Williams et al. |
| 6,585,994 | B2 | 7/2003 | Williams et al. |
| 6,610,764 | B1 | 8/2003 | Martin et al. |

(Continued)

FOREIGN PATENT DOCUMENTS

EP    0 628 586    12/1994

(Continued)

OTHER PUBLICATIONS

Galatz, et. al., "The outcome and repair integrity of completely arthroscopically repaired large and massive rotator cuff tears", *J. Bone Joint Surg. Am.*, 86-A(2):219-24 (2004).

(Continued)

*Primary Examiner* — Susan Tran
(74) *Attorney, Agent, or Firm* — Pabst Patent Group LLP

(57) ABSTRACT

Continuous processing methods for making absorbable polymeric non-wovens with one or more of the following properties: high burst strength, fine fibers of average diameter from 1 μm to 50 μm, and thickness from 10 μm to 50 mm, have been developed. Improved fiber cohesion is made possible by allowing the fibers of the non-woven to initially remain molten during web collection. In the preferred embodiment, the polymer is a polyhydroxyalkanoate, and in the most preferred embodiment, the polymer comprises 4-hydroxybutyrate. A particularly preferred embodiment is a non-woven of poly-4-hydroxybutyrate or copolymer thereof, wherein the non-woven has a burst strength greater than 0.1 Kgf, wherein the non-woven is derived by a continuous melt-blown process. The non-wovens can be used for a variety of purposes including fabrication of medical devices.

13 Claims, 1 Drawing Sheet

U.S. PATENT DOCUMENTS

| | | | |
|---|---|---|---|
| 6,623,748 B2 | 9/2003 | Clokie et al. | |
| 6,645,618 B2 * | 11/2003 | Hobbs et al. | 428/359 |
| 6,828,357 B1 | 12/2004 | Martin et al. | |
| 6,838,493 B2 | 1/2005 | Williams et al. | |
| 6,867,247 B2 | 3/2005 | Williams et al. | |
| 6,867,248 B1 | 3/2005 | Martin et al. | |
| 6,878,758 B2 | 4/2005 | Martin et al. | |
| 6,905,987 B2 | 6/2005 | Noda et al. | |
| 7,025,980 B1 | 4/2006 | Williams et al. | |
| 7,179,883 B2 | 2/2007 | Williams et al. | |
| 7,244,442 B2 | 7/2007 | Williams et al. | |
| 7,268,205 B2 | 9/2007 | Williams et al. | |
| 2002/0132546 A1 * | 9/2002 | Yamanaka et al. | 442/400 |
| 2003/0211131 A1 * | 11/2003 | Martin et al. | 424/426 |
| 2004/0234576 A1 | 11/2004 | Martin et al. | |
| 2006/0058470 A1 | 3/2006 | Rizk et al. | |
| 2007/0071790 A1 * | 3/2007 | Ameer et al. | 424/423 |
| 2007/0198087 A1 | 8/2007 | Coleman et al. | |

FOREIGN PATENT DOCUMENTS

| | | |
|---|---|---|
| WO | WO 95/33874 | 12/1995 |
| WO | WO 99/32536 | 7/1999 |
| WO | WO 00/51662 | 9/2000 |
| WO | WO 00/56376 | 9/2000 |
| WO | WO 01/32229 | 5/2001 |
| WO | WO 2004/101002 | 11/2004 |
| WO | WO 2004101002 A2 * | 11/2004 |
| WO | WO 2006/015276 | 2/2006 |
| WO | WO 2007/092464 | 8/2007 |
| WO | WO 2008/008068 | 1/2008 |

OTHER PUBLICATIONS

Hori, et al., "Chemical synthesis of high molecular weight poly(3-hydroxybutyrate-co-4-hydroxybutyrate)", *Polymer*, 36(24): 4703-4705 (1995).

Ito and Morioka, "Surgical treatment for large and massive tears of the rotator cuff", *Int. Orthop.*, 27(4):228:31 (2003).

Martin, et al., "Medical applications of poly-4-hydroxybutyrate: A strong flexible absorbable biomaterial", *Biochem. Eng. J.*, 16(2): 97-105 (2003).

Mura, et al., "Biomechanical effect of patch graft for large rotator cuff tears: a cadaver study", *Clin. Orthop. Relat. Res.*, (415):131-8 (2003).

Steinbüchel and Valentin, "Diversity of Bacterial Polyhydroxyalkanoic Acids", *FEMS Microbial. Lett.*, 128(3): 219-228 (1995).

Steinbüchel, "Polyhydroxyalkanoic acids", *Biomaterials*, 123-213 (1991).

"Tepha Announces Submission of Device Master File to FDA" retrieved from http://www.pressreleases.be/script_UK/newsdetail.asp?ndays+m$ID=695 on Dec. 17, 2004.

Williams and Martin, "Applications of PHAs in Medicine and Pharmacy", in *Biopolymers*, vol. 4, Polyesters III—Applications and Commercial Products, Dio and Steinbuchel (eds), Wiley-VCH: pp. 91-127 (2002).

* cited by examiner

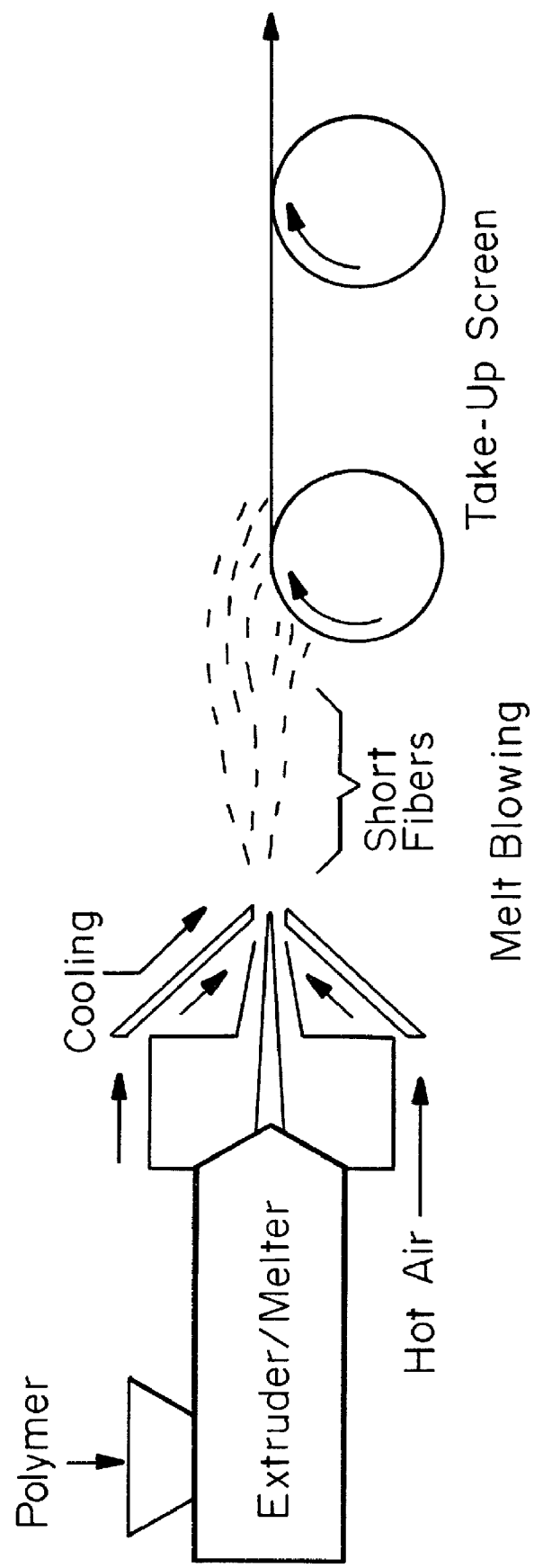

MEDICAL DEVICES CONTAINING MELT-BLOWN NON-WOVENS OF POLY-4-HYDROXYBUTYRATE AND COPOLYMERS THEREOF

CROSS-REFERENCE TO RELATED APPLICATIONS

This application claims priority to U.S. Ser. No. 61/014,906 entitled "Medical Devices Containing Melt-Blown Non-Wovens of Poly-4-Hydroxybutyrate and Copolymers" by David P. Martin, Said Rizk, Kicherl Ho, and Simon F. Williams, filed on Dec. 19, 2007.

FIELD OF THE INVENTION

The present invention generally relates to polymeric compositions that can be processed into melt-blown non-wovens using continuous processes. The compositions include polymers or copolymers containing 4-hydroxybutyrate, which can be processed into non-wovens that have high burst strength.

BACKGROUND OF THE INVENTION

Poly-4-hydroxybutyrate (P4HB, TephaFLEX® biomaterial) is a strong, pliable thermoplastic polyester that, despite its biosynthetic route, has a relatively simple structure

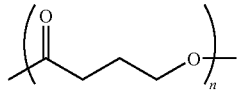

The polymer belongs to a larger class of materials called polyhydroxyalkanoates (PHAs) that are produced by numerous microorganisms (see, for example, Steinbüchel A., et al. Diversity of Bacterial Polyhydroxyalkanoic Acids, *FEMS Microbial. Lett.* 128:219-228 (1995)). In nature these polyesters are produced as storage granules inside cells, and serve to regulate energy metabolism, PHAs are also of commercial interest because of their thermoplastic properties, and relative ease of production. Several biosynthetic routes are currently known to produce P4HB. Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Lexington, Mass.). Chemical synthesis of P4HB has been attempted, but it has been impossible to produce the polymer with a sufficiently high molecular weight that is necessary for most applications (Hori, Y., et al., *Polymer* 36:4703-4705 (1995)). Copolymers of P4HB include 4-hydroxybutyrate copolymerized with 3-hydroxybutyrate or glycolic acid (U.S. patent application No. 20030211131 by Martin and Skraly, U.S. Pat. No. 6,316,262 to Huisman et al., and U.S. Pat. No. 6,323,010 to Skraly et al.). Methods to control molecular weight of PHA polymers are described in U.S. Pat. No. 5,811,272 to Snell et al.

U.S. Pat. No. 6,245,537 to Williams et al., U.S. Pat. No. 6,623,748 to Clokie, and U.S. Pat. No. 7,244,442 to Williams et al. describe methods of making PHAs with little to no endotoxin, which is suitable for medical applications. U.S. Pat. Nos. 6,548,569, 6,838,493, 6,867,247, 7,268,205, and 7,179,883 to Williams et al. describe use of PHAs to make medical devices. PHAs with controlled degradation and degradation in vivo of less than one year are described in U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III,* 4:91-127 (2002), and by Martin, D. et al. Medical Applications of Poly-4-hydroxybutyrate: A Strong Flexible Absorbable Biomaterial, *Biochem. Eng. J.* 16:97-105 (2003). Medical devices and applications of P4HB have also been disclosed by WO 00/56376 to Williams et al. Several patents including U.S. Pat. Nos. 6,555,123, 6,585,994, and 7,025,980 describe the use of PHAs in tissue repair and engineering. WO 04/101002 to Martin et al. discloses monofilament and multifilament knitted meshes of P4HB produced by knitting monofilament and multifilament fibers of P4HB.

In February 2007, Tepha obtained FDA approval to market P-4HB sutures, the first approval of a new medical polymer in decades. The TephaFLEX® Absorbable Suture has mechanical and biological properties that are uniquely applicable to implantable medical devices when compared to conventional synthetic and biologically derived polymers. Compared to synthetic polymers such as polylactic acid (PLA) and polyglycolic acid (PGA), TephaFLEX® material is tougher and more flexible with an absorption rate and degradation profile that are compatible with human tissue repair and replacement applications. However, unlike other biopolymers such as collagen and hyaluronate, TephaFLEX® polymer is a thermoplastic and can be fabricated into virtually any shape or form—including fibers, films, tubes, foams, textiles, microspheres, and molded constructs—using a wide range of conventional melt and solvent processing techniques.

In the practice of surgery, absorbable medical textiles are used in a number of applications including hernia repair, hemostasis, and soft tissue support. These products often consist of a woven or knitted design. Non-woven textiles, on the other hand, are made of a random collection of fibers. They are not typically used in these applications due to their lower strength and the loose nature of the fibers. Non-woven materials have been used, however, to create tissue engineering constructs. As such, there currently exists a need for absorbable non-wovens with improved performance. These non-wovens can be used, for example, to reinforce tissue structures, and to serve as tissue engineering scaffolds. They may also be used as components of other devices. A number of other absorbable materials have been used to produce non-wovens for medical application. For example, non-wovens have been made from polyglycolic acid (PGA) or copolymers containing lactic acid. These materials do not, however, have ideal properties for many surgical procedures and applications. Non-wovens made from polyglycolic acid break down too rapidly for many applications, and release acidic degradation productions that can cause inflammatory reactions. Additionally, non-wovens made from PGA, PLA and their copolymers have traditionally been made by cutting and carding felting techniques from staple fibers (i.e. short fibers) not from continuous fibers. The fibers in these types of non-wovens are held together by fiber entanglement and cohesion and thus the resulting felts have low cohesive strength, resulting in low burst strengths for the non-woven felts.

It is an object of the present invention to provide methods to produce non-wovens of absorbable polymers that have relatively high burst strengths and whose fibers are bonded together for improved cohesive strength.

It is a further object of the present invention to provide continuous processes to produce such non-wovens, such as melt blowing processes, as compared to melt extrusion of fibers followed by batch processes such as cutting, carding and needling (used to prepare staple non-wovens).

It is another object of the present invention to provide non-wovens which are biocompatible and can be used in medical applications, for example, as implants such as devices for temporary tissue support, devices or components of devices for tissue in-growth and tissue engineering, as wells as porous absorbable implants for delivery of therapeutic agents or materials.

It is yet another object of the invention to provide continuous processes for polymer non-woven production which yield materials with excellent physical and mechanical properties.

SUMMARY OF THE INVENTION

Continuous processing methods for making absorbable polymeric non-wovens with one or more of the following properties; burst strength greater than 0.1 Kgf, high toughness, low modulus, and thickness from 10 µm to 5 mm, have been developed. The non-wovens have unexpectedly good cohesion of the fibers in the non-wovens due to fusion of the fibers, which remain molten, during the web collection process. In the preferred embodiment, the polymer is a polyhydroxyalkanoate, and in the most preferred embodiment, the polymer contains 4-hydroxybutyrate. A particularly preferred embodiment is a non-woven of poly-4-hydroxybutyrate or copolymer thereof, wherein the non-woven contains fine fibers with average diameters ranging from 1 µm to 50 µm, and wherein the non-woven is derived by melt-blown processing with an extrusion temperature between 60 and 275° C., and a high velocity air temperature between 100 and 300° C. for polymer strand attenuation.

The non-wovens can be used for a variety of purposes including fabrication of medical devices, particularly implantable medical devices. For example, the non-wovens may be used to make partially or fully absorbable biocompatible medical devices, or components thereof.

BRIEF DESCRIPTION OF THE DRAWINGS

FIG. 1 is a diagram of the melt blowing process to manufacture non-woven materials from synthetic polymers. (From Celanese Acetate LLC, "Complete Textile Glossary.")

DETAILED DESCRIPTION OF THE INVENTION

Definitions

"Poly-4-hydroxybutyrate" as generally used herein means a homopolymer comprising 4-hydroxybutyrate units. It may be referred to herein as P4HB or TephaFLEX® biomaterial (manufactured by Tepha, Inc., Lexington, Mass.).

"Copolymers of poly-4-hydroxybutyrate" as generally used herein means any polymer containing 4-hydroxybutyrate with one or more different monomer units. In a preferred embodiment, the different monomer unit is one or more hydroxy acid monomer units.

"Bicomponent" as generally used herein means a non-woven containing two thermoplastic materials.

"Blend" as generally used herein means a physical combination of different polymers, as opposed to a copolymer containing of two or more different monomers.

"Burst strength" as used herein is determined by test method ASTM D6797-02 "Standard test method for bursting strength of fabrics constant rate of extension (CRE) ball burst test," using a MTS Q-Test Elite universal testing machine, or similar device. The testing fixture uses a one-inch diameter ball and a 1.75-inch diameter circular opening. Non-woven samples are tested with a pre-load setting of 0.05 Kg, and a ball rate of 305 mm/minute until failure.

"Tensile modulus" is the ratio of stress to strain for a given material within its proportional limit.

"Toughness", as used herein, refers to a property of a material by virtue of which it can absorb energy; the actual work per unit volume or unit mass of material that is required to rupture it. Toughness is usually proportional to the area under the load-elongation curve such as the tensile stress-strain curve. (Rosato's Plastics Encyclopedia and Dictionary, Oxford Univ. Press, 1993.)

"Elongation" or "extensibility" of a material means the amount of increase in length resulting from, as an example, the tension to break a specimen. It is expressed usually as a percentage of the original length. (Rosato's Plastics Encyclopedia and Dictionary, Oxford Univ. Press, 1993.)

"Molecular weight" as used herein, unless otherwise specified, refers to the weight average molecular weight (Mw), not number average molecular weight (Mn).

"Absorbable" as generally used herein means the material is broken down in the body and eventually eliminated from the body within five years.

"Biocompatible" as generally used herein means the biological response to the material or device being appropriate for the device's intended application in vivo. Any metabolites of these materials should also be biocompatible.

"Non-woven" as generally used herein refers to a manufactured construct that is made of a randomly aligned collection of fibers that are bonded by cohesion and/or adhesion, as opposed to knitted or woven constructs in which the fibers or threads are wrapped around one another in a regular fashion. In the case of the P4HB non-woven, the fibers may be fused to one another during the manufacturing process.

"Melt processing" as generally used herein refers to a thermal process in which a material is melted, formed into a shape and then cooled to retain a desired shape. For example, typical melt processing techniques include melt extrusion and injection molding.

Composition

Methods have been developed to produce non-wovens of P4HB and copolymers thereof with high burst strength. These methods may be used to prepare non-wovens with fine fibers ranging in average diameter from 1 µm to about 50 µm. The methods may be run directly and continuously, which is particularly advantageous in manufacturing, unlike the formation of traditional needle punched non-wovens that are prepared batch wise through multiple processing steps (such as crimping, cutting, carding, needling, etc.). The P4HB non-wovens can be prepared by melt-blown processing.

A. Polymers

The processes described herein can typically be used with poly-4-hydroxybutyrate (P4HB) or a copolymer thereof. Copolymers include P4HB with 3-hydroxybutyrate, and P4HB with glycolic acid monomer. P4HB and copolymers thereof can be obtained from Tepha, Inc. of Lexington, Mass. Other absorbable polymers may be included in the process, such as polyglycolic acid ("PGA") and/or polylactic acid ("PLA"), to produce bicomponent non-wovens, wherein the added polymer imparts improved performance such as more rapid degradation rate, higher surface area, greater loft or thickness of the non-woven, and combinations thereof. Additionally, other non-absorbable polymers, such as polypropylene or polyethylene terephthalate, may be included to produce bicomponent non-wovens, wherein the added polymer imparts improved performance such as prolonged strength retention. In a preferred embodiment, the non-wovens can be prepared from PHA materials.

The Mw (typically this is measured as the weight average of the polymers and is expressed in Daltons, for example, as determined by GPC relative to a standard such as polystyrene) of the polymers used should be selected so as to provide a non-woven construct of uniform consistency without significant degradation of the polymer. The Mw may depend on the polymer used as different polymers have varying potential to make uniform fibers based on their differing melt viscosities at the desired processing temperature. For instance, a Mw of 200,000 (by GPC relative to polystyrene) may be appropriate for preparing a melt-blown nonwoven from P4HB, while a lower Mw (MFI 1,800, 230° C./12.16 kg) is typically more appropriate for preparing melt blown non-wovens from polypropylene.

B. Non-Wovens

In a preferred embodiment, non-wovens can be prepared with thicknesses of less than 50 mm, but greater than 10 µm. More preferably the thickness is between 50 µm and 3 mm. It has been discovered that non-wovens of P4HB polymer or copolymers thereof can be prepared with unexpectedly high burst strengths. Unexpectedly high cohesion of the fibers within the non-woven can be achieved by keeping the fibers molten during the web collection process leading to improved fusion of the fibers at their crossover points. Burst strengths exceed 0.1 Kgf, and more preferably exceed 0.75 Kgf. With appropriate choice of extrusion temperature, screw speed, die collector distance (DCD), die hole size, number of holes in die, high velocity air temperature for polymer strand attenuation, and polymer molecular weight, high burst strength non-wovens comprising fine fibers with average diameters of 1 µm to 50 µm can be prepared. For example, melt-blown non-wovens of P4HB with a thickness of 0.108 mm can be prepared with a burst strength of 0.75 Kgf. Increasing the thickness to 0.295 mm increases the burst strength to 4.1 Kgf.

Burst strength of the non-wovens can be determined by ASTM D6797-02, Standard Test Method for Bursting Strength of Fabrics Constant-Rate-of-Extension (CRE) Ball Burst Test. The testing fixture comprises a 1-inch diameter ball, and a fixture with a 1.75-inch diameter circular opening. The non-woven samples are tested using a universal testing machine, for example, a Q-Test Elite by MTS, with a pre-load setting of 0.05 Kg, and a ball rate set at 305 mm/minute until failure. The ball is pushed through the sample at a constant rate and force over extension curve is recorded. Breaking load (Kgf), elongation at break (mm) and location of break are recorded.

C. Other Components

The P4HB polymer and copolymer non-wovens may contain other materials including, but not limited to, plasticizers, nucleants, other polymers, additives, and compatibilizers. Examples of plasticizers are disclosed in U.S. Pat. No. 6,905,987 to Noda et al. Other components may be added to impart benefits such as, but not limited to, increased stability, including oxidative stability, brightness, color, flexibility, resiliency, workability, processibility (by addition of processing aids), and viscosity modifiers.

In addition to adding other components directly to the P4HB polymer or copolymer thereof, it is also possible to prepare bicomponent non-wovens of P4HB or its copolymers. These bicomponent non-wovens can be prepared by melt-blowing at least two materials simultaneously. Exemplary materials include hydrogels and water soluble polymers.

Active components, including therapeutic, diagnostic and/or prophylactic agents, or other substances may be incorporated into the non-wovens, either at the time of melt blowing, or in a later processing step. Such compositions may be used for controlled release of the drugs or other substances or may be used to modify the performance of the non-woven material. Exemplary active agents include, but are not limited to, proteins, peptides, sugars, polysaccharides, glycoproteins, lipids, lipoproteins, nucleic acid molecules, inorganic or organic synthetic molecules, and combinations thereof. Examples of materials to be incorporated include hemostatic agents, anti-adhesive agents (i.e., preventing or decreasing scarring), antibodies, growth factors, cytostatic agents, and cytotoxic agents. The non-wovens may contain cells, proteins, or other substances including allograft and xenograft materials. It may be advantageous to incorporate contrast agents, radiopaque markers, or radioactive substances.

For certain applications it may also be desirable to incorporate fillers, including materials such as titanium dioxide, calcium carbonate, hydroxyapatite, and/or tricalcium phosphate.

D. Formation into Devices

Non-wovens made from P4HB polymers and copolymers thereof by melt-blown processes are characterized by their formation from fine fibers with average diameters ranging from 1 µm to about 50 µm. These non-wovens are also characterized by their high burst strengths, exceeding 0.1 Kgf. These non-wovens have properties that are substantially improved for many medical applications relative to PGA-based non-wovens.

The non-wovens possess properties that are desirable in preparing medical products, particularly implantable medical devices. For example, the non-wovens may be used to make partially or fully absorbable biocompatible medical devices, or components thereof. Such devices include, but are not limited to: stent, stent graft, stent coating, drug delivery device, device for temporary wound or tissue support, repair patch, tissue engineering scaffolds, retention membranes (for example, to retain bone graft), anti-adhesion membrane, tissue separation membrane, hernia repair device, device coating (including devices to improve fixation), cardiovascular patch, vascular closure device, sling, biocompatible coating, rotator cuff repair device, meniscus repair device, adhesion barrier, guided tissue repair/regeneration device, articular cartilage repair device, nerve guide, tendon repair device, intracardiac septal defect repair device, including but not limited to atrial septal defect repair devices and PFO closure devices, left atrial appendage (LAA) closure device, pericardial patch, bulking and filling agent, vein valve, heart valve, bone marrow scaffold, meniscus regeneration device, ligament and tendon graft, ocular cell implant, spinal fusion device, imaging device, skin substitute, dural substitute, bone graft substitute, wound dressing, and hemostat.

Methods of Manufacturing Non-Wovens

A. Method of Making P4HB Polymer or Copolymer Non-Wovens by Melt-Blowing

A schematic drawing for a melt blowing apparatus is shown in FIG. 1. To prepare a melt blown non-woven from P4HB, the molten polymer is conveyed to the melt blowing die by a screw extruder. At the die, the polymer is extruded through a many small holes to create a plurality of polymer filaments. These polymer filaments are stretched and attenuated by a stream of hot air and are accelerated toward the collection belt. Depending upon the processing conditions and the temperature and velocity of the air used to attenuate the fibers, the fibers may break into shorter filaments (as shown in the SEMs shown in FIGS. 2A-E), or may remain intact to form longer, continuous filaments. During the stretching process, the fibers may entangle to form a random collection of filaments as they impact the moving collection drum called the take up screen or collector, see FIGS. 2A-2E. If the fibers remain molten prior to hitting the collector, the fibers may fuse on the collection belt. (Note: For many polymers, such as polypropylene, the fibers crystallize very rapidly after exiting the melt blowing die. As such, they solidify during attenuation and do not fuse on the collector. Thus the non-woven material is made of loosely entangled fibers with low cohesive strength, as opposed to a more cohesive mesh of fused fibers.) After cooling, the non-woven material is removed from the take up screen and may be collected on a separate take up roll.

In a preferred method, a non-woven of P4HB polymer or copolymer may be prepared as follows. The P4HB polymer is fed into a 1-inch single screw extruder. Temperatures are adjusted from 60-275° C., and more preferably from 150-240° C., to gradually melt the polymer as it feeds into the melt-blowing die. Higher temperatures are necessary to extrude higher molecular weight polymer. The die size may be selected according to the need. In a preferred method, the die is six inches in width and is oriented perpendicular to the take up direction of the collector. The extruder (or melt pump) conveys the P4HB polymer into a channel that narrows to a spinneret consisting of a row, or multiple rows, of holes, usually on the order of 10-100 holes per inch. In a preferred method, the six-inch die has 120 holes with a hole size of 0.010 inches. The extruded polymer strands are attenuated by heated high velocity air that converges on the die tip, as shown in FIG. 1. In a preferred method, the air is heated to 100-300° C., and more preferably to 180-240° C.

The fibers that form are extremely fine, and are blown onto a moving collector screen to form the non-woven. The distance between the die and the collector screen may be adjusted (die collector distance, DCD). In a preferred method, the die collector distance is set at 3-36 inches, and more preferably at 8 to 27 inches. The extruder speed (rpm) may also be varied to produce different non-woven configurations. In a preferred method, the extruder speed is set at 20-60 rpm, and more preferably 30-45 rpm, depending on the desired mass flow of polymer through the die. A number of parameters can be varied to control the non-woven thickness, density and fiber sizes including, but not limited to, the extruder speed, extruder temperature(s), polymer molecular weight, die configuration and hole spacing, number and size of holes, temperature of the high velocity air, quenching temperature, distance between the die and collector screen, and the speed of travel of the collector screen.

The present invention will be further understood by referenced to the following non-limiting example.

EXAMPLE 1

Preparation of P4HB Non-Woven by Melt-Blowing

P4HB (Tepha, Inc., Lexington, Mass.) (Mw 150,000) was ground into small pieces (3 mm) using a Fritsch cutting mill (Pulversette 15, 10 mm bottom sieve) and dried under vacuum overnight to less than 0.01% (w/w) water. The equipment used consisted of a 6" melt-blowing die fed by a 1" single screw extruder. The die was configured with 120 holes of 0.018" diameter. The die tip was set back 0.030" from the face of the die and used a 0.030" air gap. The processing parameters are shown in Table 1.

It was found that a melt temperature of about 400° F., and air temperature of 370° F., provided a good web of fibers. Once these conditions were established, the extruder screw speed (rpm) and collector position (DCD, die collector distance, in) were varied to produce several different non-woven configurations. These include a non-woven mixing larger and small fibers, with small interstitial spacing; a highly porous (interstitial spacing of 500 microns or more) non-woven mixture of larger fibers, fused at intersecting points; a porous non-woven of intermediate size fibers and intermediate interstitial spacing (less than 500 microns); a mesh of smaller fibers fused at intersecting points (interstitial spacing significantly less than 500 microns); and a non-woven mesh in which the fibers are substantially aligned, having interstitial spacing of less than 500 microns.

TABLE 1

Processing parameters for the 6" melt blowing line at TANDEC used to produce P4HB non-woven materials in Example 1.

| | Extruder Temperature (° F.) | | | Die Temperature (° F.) | | | | Air Temperature (° F.) | | | | | | Extruder |
| --- | --- | --- | --- | --- | --- | --- | --- | --- | --- | --- | --- | --- | --- | --- |
| Sample | Zone 1 | Zone 2 | Zone 3 | Zone 8 | Zone 9 | Zone 10 | Zone 11 | Heater 1 | Heater 2 | Die Exit | DCD Inch | % Air | Speed rpm |
| 1 | 380 | 420 | 430 | 418 | 404 | 387 | 410 | 386 | 431 | 400 | 5 | 15 | |
| 2 | 370 | 410 | 420 | 423 | 404 | 401 | 410 | 386 | 430 | 400 | 25 | 35 | |
| 6 | 380 | 410 | 410 | 415 | 400 | 398 | 410 | 220 | 268 | 360 | 12 | 25 | |
| 8 | 360 | 380 | 400 | 417 | 404 | 400 | 400 | 331 | 392 | 370 | 12 | 6 | |
| 9 | 360 | 400 | 400 | 418 | 402 | 400 | 400 | 332 | 392 | 360 | 12 | 12 | |
| 11 | 380 | 400 | 420 | 419 | 404 | 403 | 400 | 331 | 391 | 370 | 12 | 5 | 45 |
| 12 | 380 | 400 | 420 | 414 | 404 | 403 | 400 | 331 | 391 | 370 | 12 | 5 | 31 |
| 13 | 380 | 400 | 420 | 419 | 404 | 403 | 400 | 331 | 391 | 370 | 8 | 5 | 31 |
| 14 | 380 | 400 | 420 | 419 | 404 | 403 | 400 | 331 | 341 | 370 | 27 | 5 | 31 |

Several melt-blown non-woven samples were prepared. The average fiber diameters for these samples were determined using a calibrated microscope and the data are shown in Table 2. As can be seen from Tables 1 and 2, the fiber diameter depends upon the processing conditions such as extruder speed and DCD.

The fibers become fused at their cross-over points and this leads to improved cohesion of the fibers albeit a stiffer mesh than would result from a needle punched non-woven. Fusion of the fibers occurs because the P4HB fiber remains molten during the web collection.

TABLE 2

Fiber diameter data from selected processing conditions for P4HB melt-blown non-woven.

|  | Sample | | | | |
| --- | --- | --- | --- | --- | --- |
|  | 10 | 11 | 12 | 13 | 14 |
| Extruder Speed (rpm) | — | 45 | 31 | 31 | 31 |
| DCD | 12 | 12 | 12 | 8 | 27 |
| Fiber Diam. (avg) | 21.96 | 49.50 | 20.85 | 18.68 | 15.41 |
| Fiber Diam. (Std. Dev.) | 14.26 | 20.69 | 5.77 | 5.34 | 3.84 |

EXAMPLE 2

Preparation of P4HB Non-Woven by Melt-Blowing

Melt blown non-woven fabrics of P4HB were made as in example 1, but using pellets of higher Mw (400,000 daltons weight average molecular weight). The die was configured with 121 holes of 0.010" diameter. The die tip was set back 0.060" from the face of the die and used a 0.060" air gap. The processing parameters are shown in Table 3. It was found that a melt temperature of about 230° C., and air temperature of 230° C. provided a good web of fibers. Once these conditions were established, the collector speed was varied to collect non-wovens of various thicknesses. The properties of several sample non-wovens are shown in Table 4.

TABLE 3

Processing parameters for the 6" melt blowing line at TANDEC used to produce P4HB non-woven materials in Example 2.

| Extruder | | | | | Ambient | Die | | | Attenuation Air | | | |
| --- | --- | --- | --- | --- | --- | --- | --- | --- | --- | --- | --- | --- |
| Zone 1 Deg C. | Zone 2 Deg C. | Zone 3 Deg C. | Connector Deg C. | Speed RPM | Air Temp Deg C. | Zone 2 Deg C. | Zone 3 Deg C. | Zone 4 Deg C. | Press. PSI | Press. PSI | Temp. Deg C. | DCD Mm |
| 144.7 | 202.9 | 234 | 229.7 | 2 | 33.5 | 248.3 | 228.4 | 238.5 | 700 | 3 | 230 | 630 |

TABLE 4

Properties of melt-blown non-wovens prepared in Example 2.

| Sample | | Thickness | Unit Weight | Ball Burst |
| --- | --- | --- | --- | --- |
| Roll # | Sample # | Mm | gm/m^2 | kgf |
| 1 | 10 | 0.166 | 64.6 | 2.911 |
| 2 | 5 | 0.114 | 38.5 | 1.549 |

Modifications and variations of the methods and compositions will be apparent from the foregoing detailed description and are intended to come within the scope of the appended claims.

We claim:

1. A non-woven comprising fibers of poly-4-hydroxybutyrate or copolymer thereof having a weight average molecular weight greater than 50,000 g/mol,
the fibers having an average diameter of from about 1 μm to about 50 μm,
wherein the non-woven has a burst strength greater than 0.1 Kgf, and
wherein the non-woven is derived by a melt blown process comprising
melt extruding a poly-4-hydroxybutyrate or copolymer polymer at a temperature between 60° C. and 275° C.,
conveying the poly-4-hydroxybutyrate or copolymer into a multiple hole spinneret, and
attenuating the extruded polymer strands with high velocity air at a temperature of 100-300° C.

2. The non-woven of claim 1 wherein the non-woven has a thickness of 10 μm to 5 mm.

3. The non-woven of claim 1 wherein the fibers of the non-woven fused together during web collection.

4. The non-woven of claim 1 formed into a device.

5. The non-woven of claim 4 in the form of a device or component of a device selected from the group consisting of a stent, stent graft, stent coating, drug delivery device, device for temporary wound or tissue support, repair patch, tissue engineering scaffold, retention membrane, anti-adhesion membrane, tissue separation membrane, hernia repair device, device coating, cardiovascular patch, catheter balloon, vascular closure device, sling, biocompatible coating, rotator cuff repair device, meniscus repair device, adhesion barrier, guided tissue repair/regeneration device, articular cartilage repair device, nerve guide, tendon repair device, intracardiac septal defect repair device, left atrial appendage (LAA) closure device, pericardial patch, bulking and filling agent, vein valve, heart valve, bone marrow scaffold, meniscus regeneration device, ligament and tendon graft, ocular cell implant, spinal fusion device, imaging device, skin substitute, dural substitute, bone graft substitute, wound dressing, and hemostat.

6. The non-woven of claim 1 wherein the non-woven is a bi-component non-woven, further comprising a second thermoplastic polymer.

7. The non-woven of claim 1 further comprising one or more prophylactic, diagnostic, or therapeutic agents.

8. The non-woven of claim 7 wherein the diagnostic agents are selected from the group consisting of radiolabelled substances, imaging agents, radiopaque markers, and contrast agents.

9. The non-woven of claim 1 further comprising one or more materials selected from the group consisting of other polymers, protein, plasticizers, nucleants, compatibilizers, porogens, anti-oxidants, dyes, viscosity modifiers, and odor control agents.

10. A method of producing a non-woven of poly-4-hydroxybutyrate or copolymer thereof, wherein the non-woven comprises fine fibers having an average diameter of from about 1 μm to about 50 μm, and a burst strength greater than 0.1 Kgf, comprising
deriving the non-woven by melt-blown processing of the polymer by melt extrusion at a temperature between 60° C. and 275° C.,
conveying the poly-4-hydroxybutyrate or copolymer into a multiple hole spinneret, and
attenuating the extruded polymer strands with high velocity air at a temperature of 100-300° C., wherein the poly-4-hydroxybutyrate or copolymer has a weight average molecular weight greater than 50,000 g/mol.

11. The method of claim 10 comprising forming a non-woven while the fibers are molten, wherein the fibers fuse at their crossover points as the polymer solidifies.

12. The method of claim 10 further comprising forming the non-woven into a device or component of a device selected from the group consisting of a stent, stent graft, stent coating, drug delivery device, device for temporary wound or tissue support, repair patch, tissue engineering scaffold, retention membrane, anti-adhesion membrane, tissue separation membrane, hernia repair device, device coating, cardiovascular patch, catheter balloon, vascular closure device, sling, biocompatible coating, rotator cuff repair device, meniscus repair device, adhesion barrier, guided tissue repair/regeneration device, articular cartilage repair device, nerve guide, tendon repair device, intracardiac septal defect repair device, left atrial appendage (LAA) closure device, pericardial patch, bulking and filling agent, vein valve, heart valve, bone marrow scaffold, meniscus regeneration device, ligament and tendon graft, ocular cell implant, spinal fusion device, imaging device, skin substitute, dural substitute, bone graft substitute, wound dressing, and hemostat.

13. A method of using the device of claim 12, comprising implanting or administering the device at a site in or on a patient in need thereof.

* * * * *